United States Patent [19]

Lovering et al.

[11] 4,180,616

[45] Dec. 25, 1979

[54] SOFT SOLDERING

[75] Inventors: David G. Lovering; James H. Turnbull, both of Swindon, England

[73] Assignee: Multicore Solders Limited, Hertfordshire, England

[21] Appl. No.: 854,702

[22] Filed: Nov. 25, 1977

[30] Foreign Application Priority Data

Nov. 25, 1976 [GB] United Kingdom ............... 49284/76

[51] Int. Cl.$^2$ ............................................. B23K 35/34
[52] U.S. Cl. ..................................... 428/389; 148/24; 148/23
[58] Field of Search .................................. 148/23–25; 428/389

[56] References Cited

U.S. PATENT DOCUMENTS

| | | | |
|---|---|---|---|
| 3,293,742 | 12/1966 | Chmelik | 148/23 |
| 3,567,432 | 3/1971 | Wardell | 148/23 |
| 3,734,791 | 5/1971 | Poliak | 148/23 |
| 3,865,641 | 2/1975 | Aronberg | 148/23 |

*Primary Examiner*—P. D. Rosenberg
*Attorney, Agent, or Firm*—Browdy and Neimark

[57] ABSTRACT

Flux compositions for use in soft soldering processes comprise as part or all of the active flux material at least one compound selected from the class of compounds characterized by the presence therein of a perhydro-1,2-cyclopentanophenanthrene ring system. Compounds belonging to this class include the bile acids.

7 Claims, No Drawings

SOFT SOLDERING

This invention relates to soft soldering and is concerned particularly but not exclusively with flux materials used in soft soldering.

Soldering with a soft solder, i.e. a tin-lead based alloy melting at below about 400° C., is widely employed in the electrical and electronics industries, for example in the assembly of printed circuits, electronic components and conductors. In order to produce a satisfactory soldered joint, it is necessary to use a flux with the soft solder in order to remove any residual surface oxide films and hence provide a clean surface and in order to reduce the surface tension of the molten solder and hence promote good wetting of the surface by the solder. Fluxes for soft soldering can be classified as corrosive, intermediate, or non-corrosive. It is normally essential in the electronics industry to use a flux which is non-corrosive, i.e. a flux which after use in a soldering operation yields a residue which is substantially inert and hence will not appreciably corrode the soldered joint particularly under humid conditions. Non-corrosive fluxes are conventionally natural rosin-based fluxes comprising wood rosin or gum rosin. Rosin (also known as colophony) principally comprises a mixture of rosin acids the major component of which is abietic acid. The rosin flux may contain a small amount of an additive, generally known as an activating agent, which will improve the fluxing action of the rosin. Such rosin fluxes may be incorporated as a core or cores in solder wires, or may be used in the form of solutions or pastes.

We have now found that another class of naturally occurring compounds possesses the capability of acting as an effective non-corrosive flux material in soft soldering and may therefore provide a partial or complete replacement for rosin in a rosin-based flux.

This class of compounds is characterized by there being present in each compound the perhydro-1,2-cyclopentanophenanthrene ring system having the basic structure:

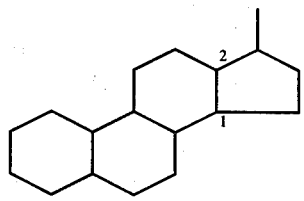

Compounds belonging to this class occur widely in plants and animals and include the sterols and the bile acids.

Thus in accordance with one aspect of the invention there is provided a method of soft soldering a first member to a second member at a joint site, said first and second members being formed from a metal or alloy capable of being soft soldered, which method comprises disposing the first and second members in positions such as to provide a joint site and thereafter providing at the joint site a soft solder alloy and a flux composition comprising as an active flux material at least one compound containing a perhydro-1,2-cyclopentanophenanthrene ring system.

Advantageously the active flux material comprises one or more bile acids (as hereinafter defined), for example cholic acid, which as with the conventional rosin-based fluxes set to a glassy, non-corrosive residue after melting. Other suitable compounds may be acid derivatives of cholesterol, for example the monophosphate, diphosphate and sulphonate derivatives.

The flux composition employed in accordance with the method of the invention may be applied directly to the surfaces of the two members to be soldered at a joint site, for example in the form of a solid, a paste or a solution, e.g. an alcoholic solution, or may be advantageously applied together with the soft solder alloy in the form of a fluxed solder composition comprising the soft solder alloy and the flux composition. The fluxed solder composition can be in the form of a flux-cored solder member such as a fluxed wire, that is an elongate member of soft solder alloy having a substantially uninterrupted core, or plurality of separate cores, of the flux composition extending longitudinally through the interior of the elongate member. Preferably the flux-cored solder wire will contain at least 5 separate cores of the flux positioned substantially symmetrically with respect to the longitudinal axis of the wire, as in the case of the rosin-cored solder wire sold by us in the United Kingdom under the label Trade Mark "ERSIN Multicore 5-Core Solder". The flux-cored solder wire can be made by extruding the solder alloy so as to form an elongate wire whilst simultaneously introducing the flux cores. It will be appreciated that for manufacturing a flux-cored solder wire by the foregoing method, the flux composition of the invention should generally comprise a flux compound having a melting point which is lower than that of the soft solder alloy from which the solder wire is formed, so that the flux composition can be introduced in a molten state into the solder alloy. Following the incorporation of the flux cores into the solder wire, the diameter of the extruded wire may be reduced by, for example, rolling or drawing.

Instead of a flux-cored solder wire, the fluxed solder composition may be in the form of a solder tape or solder preforms, such as for example washers, rings, pellets or discs, which may be punched from solder tape.

Thus in accordance with another aspect of the invention, there is provided a fluxed solder composition comprising a soft solder alloy in association with a flux composition comprising as an active flux material at least one compound containing a perhydro-1,2-cyclopentanophenanthrene ring system, advantageously, one or more bile acids and preferably cholic acid. Said compound or compounds may be the sole active flux material in the flux composition or may be partially replaced by other flux materials capable of being used in soft soldering, for example conventional rosin-based flux materials.

The soft solder alloy employed in the fluxed solder composition of the invention may be, for example, a tin/lead alloy containing at least 1% by weight of tin with the balance being lead. For instance the alloy may be a 60/40 tin/lead alloy. If desired, the alloy may also contain minor proportions of one or more other metals, for example, up to 7% antimony, up to 3% copper, up to 20% cadmium or up to 10% silver, apart from any incidental elements and/or impurities. Alternatively the soft solder alloy may be a higher melting alloy, i.e. an alloy melting above the normal melting point of conventional tin/lead alloys, for example a solder alloy containing silver or copper, such as those used as low creep solders and having melting points in the range from 200° to 300° C.

For the purposes of the present invention, a bile acid is defined as being either (1) an acid of the general formula:

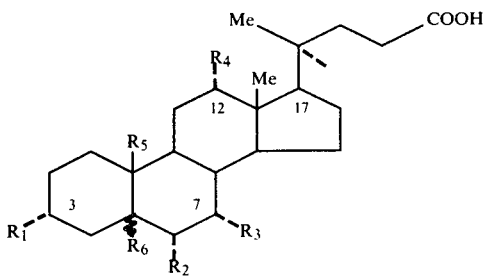

where $R_1$ to $R_4$ each represent H or OH, $R_5$ represents $CH_3$ and $R_6$ is $\beta$-H (the simple bile acids) or $R_1$ to $R_4$ each represent 2H or O, $R_5$ represents H and $R_6$ represents $\alpha$-or $\beta$-H (the ketobile acids); or (2) a conjugated bile acid, which is a peptide formed from a simple bile acid as defined in (1) and glycerine or taurine.

Exemplary simple bile acids are cholanic ($R_1=R_2=R_3=R_4=H$), cholic ($R_1=OH$; $R_2=H$; $R_3=R_4=OH$), lithocholic ($R_1=OH$: $R_2=R_3=R_4=H$), desoxycholic ($R_1=OH$; $R_2=R_3=H$; $R_4=OH$) and chenodesoxycholic ($R_1=OH$; $R_2=H$; $R_3=OH$; $R_4=H$) acids, and conjugated bile acids derived from the simple acids include glycocholic acid, glycodesoxycholic acid, taurocholic acid and taurodesoxycholic acid. The keto-bile acids include dehydrocholic ($R_1=O$; $R_2=H_2$; $R_3=R_4=O$; $R_6=\beta$-H) and dehydrodeoxycholic ($R_1=O$; $R_2=R_3=H_2$; $R_4=O$; $R_6=\beta$-H) acids.

The bile acids occur usually in the form of their sodium salt, as constituents of animal bile, which is available in large quantities from slaughterhouses and which finds few commercial uses. Animal bile generally contains a mixture of bile acid salts, the composition of the different acids varying with the animal species. For the purposes of the present invention it is clearly simpler and cheaper to use the naturally-occurring mixture of bile acids as a flux material and it is not necessary to extract a single pure acid from the mixture. In particular a bile acid salt extract which is sold commercially as "sodium choleate" may be used to prepare an acid mixture for use as a flux composition according to the present invention. The free acids are obtained from the salts by acidification, which may be effected by direct treatment with acid followed by dilution precipitation or solvent extraction, or by using ion-exchange resins or by other conventional procedures.

Regaring the acid derivatives of cholesterol, these may be simply prepared direct from cholesterol. Some of the acid derivatives are self-gelling and their preparation and application in gel form may be particularly advantageous for their use as flux materials.

The amount of flux composition used and the techniques of application to the surfaces to be soldered are comparable with the conventional procedures using rosin-based fluxes.

As with conventional practice again, there may be present in the flux composition one or more conventional flux additives such as a suitable flux activating agent to improve the fluxing activity of the active flux material, for example an amine hydrochloride, though in the case of the conjugated bile acids which possess their own amine group, this may not be required as they might be self-activating and may even, when present in admixture with non-conjugated bile acids, serve to activate the latter.

Thus in accordance with a further aspect of the invention there is provided a flux composition comprising, as an active flux material, at least one compound containing a perhydro-1,2-cyclopentanophenanthrene ring system, and an activating agent therefor.

The invention will now be illustrated by the following non-limitative Examples.

EXAMPLE 1

A mildly tarnished 24 SWG pure copper wire was warmed with a soldering iron and dipped into pure cholic acid powder, so that a small amount of the powder adhered to the surface of the wire. Non-cored 60/40 (Sn/Pb) soft solder was then applied with the soldering iron and the copper wire immediately became "tinned". The oxide coating had been effectively ruptured and clean, continuous wetting of the copper by the solder was evident.

In a similar operation the copper wire was soldered to a ⅛" wide copper foil strip and the completed joint was found to remain coated with a glassy residue of flux. This was easily removable mechanically and did not appear to be corrosive or otherwise deleterious towards the joint, and indeed, afforded some protection to the joint during cooling.

EXAMPLE 2

The procedure described in Example 1 was repeated with the cholic acid being replaced by lithocholic acid. The same results were obtained.

EXAMPLE 3

The procedure described in Example 1 was repeated with the cholic acid being replaced by desoxycholic acid The same results were obtained.

EXAMPLE 4

The procedure described in Example 1 was repeated with the cholic acid being replaced by a mixture consisting of equal parts by volume of lithocholic acid, desoxycholic acid and cholic acid. The same results were obtained.

EXAMPLE 5

A liquid flux was prepared by dissolving a mixture of 1000 mg. of cholic acid, 125 mg. of desoxycholic acid and 1 mg. of lithocholic acid in 5 ml. of boiling ethanol and evaporating part of the alcoholic solvent. The proportions of the acids in the mixture are typical of the relative proportions which would be present in a natural source of bile acids.

The flux materials described in each of the foregoing Examples can be used to solder copper wire to copper strip with either a 60/40 or 80/20 tin/lead soft solder alloy, or with such alloys containing in addition small quantities of silver and copper.

What is claimed is:

1. A soldering composition for use in soft soldering processes, the composition comprising (a) a soft solder alloy and (b) a flux composition comprising as an essential active flux material at least one compound containing a perhydro-1,2-cyclopentanophenanthrene ring system.

2. A soldering composition as claimed in claim 1, wherein said flux material is a bile acid or mixture of bile acids.

3. A soldering composition as claimed in claim 1, wherein said flux material is cholic acid.

4. A soldering composition for use in soft soldering processes, the composition comprising (a) a soft solder tin/lead alloy and (b) a flux composition comprising as an essential active flux material at least one compound containing a perhydro-1,2-cyclopentanophenanthrene ring system.

5. A soldering composition as claimed in claim 4, wherein said flux material is composed of one of more bile acids.

6. A soldering composition as claimed in claim 4, wherein said flux material is cholic acid.

7. A soldering composition as claimed in claim 1, wherein the soft solder alloy and the flux composition are maintained in interfacial contact by the soldering composition being in the form of a flux-cored solder member.

* * * * *